(12) United States Patent
Scates et al.

(10) Patent No.: US 7,902,398 B2
(45) Date of Patent: Mar. 8, 2011

(54) METHOD AND APPARATUS FOR CARBONYLATION WITH REDUCED CATALYST LOSS

(75) Inventors: Mark O. Scates, Houston, TX (US); Joshua Gregory Wagner, La Porte, TX (US)

(73) Assignee: Celanese International Corporation, Dallas, TX (US)

( * ) Notice: Subject to any disclaimer, the term of this patent is extended or adjusted under 35 U.S.C. 154(b) by 962 days.

(21) Appl. No.: 11/789,768

(22) Filed: Apr. 25, 2007

(65) Prior Publication Data

US 2008/0269518 A1 Oct. 30, 2008

(51) Int. Cl.
*C07C 51/12* (2006.01)
(52) U.S. Cl. .......................... 562/519; 562/517
(58) Field of Classification Search .................. None
See application file for complete search history.

(56) References Cited

U.S. PATENT DOCUMENTS 6,657,078 B2 * 12/2003 Scates et al. .................. 562/519
2002/0151746 A1 * 10/2002 Scates et al. .................. 562/519

* cited by examiner

*Primary Examiner* — Daniel M Sullivan
*Assistant Examiner* — Yevegeny Valenrod

(57) ABSTRACT

An apparatus and method for carbonylating a reactant, including sequestering Group VIII catalyst metal from a process stream which generally has a ppb concentration of the catalyst metal. The process stream is treated with a polymer having nitrogen-containing heterocyclic repeat units to sequester the catalyst from the stream, thus allowing valuable catalyst to be recovered and returned to the reaction mixture. An apparatus provides a resin bed downstream of the light ends column in a carbonylation process. Preferably, spent resin is regenerated with a regenerant composition compatible with the carbonylation reaction mixture so that catalyst metal can be directly recycled and the resin re-used.

30 Claims, 5 Drawing Sheets

METHOD AND APPARATUS FOR CARBONYLATION WITH REDUCED CATALYST LOSS

TECHNICAL FIELD

The present invention relates generally to an apparatus and method for producing a carbonylated product such as acetic acid or acetic anhydride, and sequestering catalyst metal that is entrained in the process stream.

BACKGROUND ART

Carbonylation processes are well known in the art. Of particular commercial significance are processes for the carbonylation of methanol to make acetic acid and processes for the carbonylation of methyl acetate to make acetic anhydride. See Applied Homogeneous Catalyst With Organometallic Compounds, Cornils et al., Ed. (Bench Edition) (Wylie, Weinheim, Federal Republic of Germany 2000), Chapter 2, Parts 2.1.2 and following, pp. 104-137.

To make acetic acid, one method of choice involves carbonylating methanol in a homogeneous reaction medium wherein rhodium is utilized as a catalyst. This method is sometimes referred to in the art generally as the Monsanto process and was developed in the 1970's. A more preferred carbonylation process is taught in U.S. Pat. No. 5,144,068 to Smith et al. In this so called "low water" process, an alcohol such as methanol is reacted with carbon monoxide in a liquid reaction medium containing a rhodium catalyst stabilized with an iodide salt, especially lithium iodide along with alkyl iodide such as methyl iodide and alkyl acetate such as methyl acetate in specified proportions. With a finite concentration of water in the reaction medium, the product is the carboxylic acid instead of, for example, the anhydride. The reaction system of the '068 patent not only provides an acid product of unusually low water content at unexpectedly favorable rates, but also exhibits unexpectedly high catalyst stability. That is, the catalyst is resistant to catalyst precipitation out of the reaction medium.

Another method of choice for carbonylating methanol involves utilizing a homogeneous iridium catalyst in the reactor. There is disclosed, for example, in U.S. Pat. No. 5,883,295, to Sunley et al. a process for the production of acetic acid comprising carbonylating with carbon monoxide methanol and/or a reactive derivative thereof, in the substantial absence of a metal promoter and/or ionic iodide co-promoter in a carbonylation reactor containing a liquid reaction composition with an iridium carbonylation catalyst, methyl iodide co-catalyst, water, acetic acid, and methyl acetate wherein there is maintained in the liquid reaction composition: (a) water at a concentration of less than 5% by weight; (b) methyl iodide in a concentration of greater than 12% by weight and (c) in the carbonylation reactor a total pressure of less than 50 bar. See also U.S. Pat. No. 5,877,348 to Ditzel et al. and U.S. Pat. No. 5,887,347 also to Ditzel et al.

One drawback of homogeneous systems is the tendency of the catalyst to form volatile species which leads to catalyst loss. See, for example, U.S. Pat. No. 5,942,460 to Garland et al. at Col. 4, lines 3 and following as well as U.S. Pat. No. 5,932,764 to Morris et al. at Col. 3, line 1 and following wherein it is stated:

. . . Preferably to prevent a significant increase in the volatility of the iridium catalyst and/or optional promoter the amount of carbon monoxide in the second liquid composition withdrawn from the second reaction zone should not be reduced too low, typically to maintain at least 20% by volume of the dissolved and/or entrained gases therein . . . .

Supported catalysts systems have been proposed to avoid excessive catalyst loss through entrainment. For example, U.S. Pat. No. 5,466,874 to Scates et al., U.S. Pat. No. 5,281,359 to Scates et al., U.S. Pat. No. 5,334,755 to Yoneda et al., U.S. Pat. No. 5,364,963 to Minami et al., U.S. Pat. No. 5,155,261 to Marston et al., U.S. Pat. No. 5,892,110 to Ramprasad et al., U.S. Pat. No. 4,127,506 to Gray et al., WIPO Publication WO 98/57918, and WIPO Publication 98-33590. A significant drawback of using supported catalyst systems in carbonylation processes has been the leaching of the catalyst from the polymer; this drawback may be avoided, at least in part, by utilizing the present invention as discussed hereinafter.

Rather than using a supported catalyst, another approach has been to sequester catalyst that is entrained in process streams by using polymeric substrates. Methods of this type are described, for example, in European Patent Specification No. 1 315 693 to Johnson Matthey, and U.S. Pat. No. 6,662,770 to Cheung et al., which describe processes employing resin beds to sequester catalyst from process streams in which the entrained catalyst is present in the parts per million range.

It has been discovered in connection with the present invention, that a convenient and effective method for recovering metal catalyst in carbonylation processes can be provided by first generating a process stream having less than 100 ppb by weight of catalyst metal, and treating the process stream with a polymer having nitrogen-containing heterocyclic repeat units. Because the catalyst is present in low concentrations, moderately sized polymer beds can be used without the need for constant replacement of the polymer. Moreover, the inventive methods and apparatus enable the reclamation and re-use of valuable catalyst which would otherwise be lost to entrainment and/or volatilization.

SUMMARY OF INVENTION

In one aspect of the invention, there is provided a carbonylation process for carbonylating a reactant in the presence of a Group VIII metal catalyst, where a process stream is generated which includes the Group VIII metal in amounts of less than 100 ppb by weight, and where the metal catalyst is sequestered from that process stream by treating it with a polymer having nitrogen-containing heterocyclic repeating units. The metal catalyst may be subsequently recovered from the polymer and recycled. In another aspect of the invention, a polymer bed is regenerated using a regenerant composition which is compatible with the carbonylation reaction mixture such that recovered catalyst can be directly recycled to the reactor from regeneration liquor, that is, there is no need to isolate the catalyst metal from the regeneration liquor prior to returning the catalyst metal to the reactor.

Further features and advantages of the present invention will become apparent from the discussion that follows.

BRIEF DESCRIPTION OF DRAWINGS

The invention is described in detail below with reference to the following drawings.

DESCRIPTION OF THE PREFERRED EMBODIMENTS

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppb and like terms refer to weight percent, parts per billion by weight and so forth, unless otherwise indicated.

"Predominantly" refers to more than 50% on a molar basis unless otherwise specified. When we refer, for example, to a vinyl pyridine or vinyl pyrrolidone polymer being predominantly in the quaternized form, we mean that more than 50 mol % of the amine functionalities of the pyridine or pyrrolidone are quaternized.

As used herein the "purified process stream" includes the process stream fed forward from the light ends column, and any subsequent purifications of the light ends process stream. It will be appreciated from the discussion which follows that any stream with a low concentration of entrained or fugitive catalyst metal may be targeted for recovery in accordance with the present invention.

Flow rates through a resin bed in bed volumes per hour (BV/hour) are calculated based on the bulk volume of resin employed by dividing the volumetric flow rate of the product through the bed by the bed volume. A stream being fed through a 20 gallon resin bed at 100 gallons per hour is being purified in the bed at a flow rate of 5 bed volumes per hour, thus having a residence time of 12 minutes in the treatment bed. Lower residence times (higher flow rates) are economically desirable since smaller beds can be used, reducing equipment costs.

The Group VIII metal catalyst component may be present in the purified process stream in amounts of less than 50 ppb by weight; but may be present in the process stream in amounts of less than 40 ppb by weight, or less than 30 ppb by weight. From 5 to 30 ppb may be readily removed in accordance with the present invention. The polymer may be selected from the group consisting of pyridine ring-containing resins, pyrrolidone ring-containing resins, or combinations thereof. Typical resins may be a crosslinked vinyl pyridine resin having a degree of crosslinking of at least about 5% (preferably 10% or more) or a vinyl pyrrolidone resin having a degree of crosslinking of at least about 5% (preferably 10% or more). An alkyl halide promoter is, for example, methyl iodide, and the reactant is methanol or a reactive derivative thereof. The Group VIII metal catalyst component comprises rhodium, iridium or combinations thereof. Preferably, the polymer is operative to remove at least 50% of the Group VIII catalyst metal from the process stream. More preferably, the polymer is operative to remove at least 75% of the Group VIII catalyst metal from the process stream such as at least 85% of the Group VIII catalyst metal from the process stream or at least 90% of the Group VIII catalyst metal from the process stream. Removal of 95% and more of the Group VIII catalyst metal from the stream is readily achieved.

Typically, the purified process stream is treated in the resin bed to remove Group VIII catalyst metal at a flow rate of at least 5 BV/hour. More preferably, the purified process stream is treated in the resin bed to remove Group VIII catalyst metal at a flow rate of at least 10 BV/hour, such as at a flow rate of at least 20 BV/hour or at a flow rate of at least 40 BV/hour. In many cases, the purified process stream is treated in the resin bed to remove Group VIII catalyst metal at a flow rate of from about 5 BV/hour to about 75 BV/hour; while in still other cases the flow rate of liquid process stream through the bed can be 5-100 BV/hour or more.

In yet another aspect of the invention, there is an improvement to processes using supported Group VIII metal catalysts of the class described in U.S. Pat. No. 5,334,755 to Yoneda et al., the disclosure of which is incorporated herein by reference. Generally, the improvement includes: (a) generating a process stream such that it has a Group VIII metal content of less than 100 ppb by weight; and (b) treating the process stream having a Group VIII metal content of less than 100 ppb by weight with a polymer comprising nitrogen-containing heterocyclic repeat units operative to sequester on the polymer the Group VIII catalyst metal present in the process stream.

In another aspect of the invention, there is provided a metal carbonylation process with catalyst metal recycle including the steps of: (a) carbonylating a carbonylatable reactant in the presence of a Group VIII metal catalyst and an alkyl halide promoter to form a carbonylated product reaction mixture; (b) supplying the reaction mixture to a flasher and generating a process stream which contains entrained Group VIII catalyst metal; (c) feeding the process stream to a purification system including a resin bed of polymer provided with nitrogen-containing heterocyclic repeat units operative to sequester on the polymer entrained Group VIII catalyst metal; (d) periodically isolating the resin bed from the purification system and regenerating the resin with a regenerant composition to recover the sequestered catalyst metal in a regeneration liquor as well as regenerate the resin. The regenerant composition preferably includes a regenerant solvent and regenerating agent selected such that regeneration liquor is compatible with the reaction mixture, so that the recovered Group VIII catalyst metal may be directly recycled to the reaction mixture with regenerant liquor. Alternatively, the recovered metal can be precipitated from the liquor and re-used.

The Group VIII catalyst metal component that is the target of the inventive sequestering system may be a rhodium and/or iridium catalyst. The rhodium metal catalyst may be added in any suitable form such that rhodium is in the catalyst solution as an equilibrium mixture including $[Rh(CO)_2I_2]^-$ anion as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the equilibrium rhodium/catalyst composition changes since less carbon monoxide is available. Rhodium precipitates as $RhI_3$, for example; details as to the form of entrained rhodium downstream of the reactor are not well understood. Iodide salts help alleviate precipitation in the flasher under so-called "low water" conditions as will be appreciated by one of skill in the art.

Iodide salts maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system a wide range of non-iodide salt precursors will react with methyl iodide to generate the corresponding co-promoter iodide salt stabilizer. For additional detail regarding iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference.

Similarly, an iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

An alkyl halide co-catalyst/promoter is generally used in combination with the Group VIII metal catalyst component. Methyl iodide is a preferred as the alkyl halide promoter. Preferably, the concentration of alkyl halide in the liquid reaction composition is in the range 1 to 50% by weight, preferably 2 to 30% by weight.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention includes generally at least a reactive section, and a purification section. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water, as well as an insoluble pyridine or pyrrolidone ring containing polymer. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed in a one step or multi-step process using a converter as well as a flash vessel as hereinafter described. The crude vapor process stream from the flasher is sent to a purification system which generally includes at least a light ends column and a dehydration column. As noted earlier, the form of any catalyst metal which is entrained to the light ends column and beyond is not well understood; however, the entrained catalyst metal is lost in conventional systems.

According to the invention, a process stream (located in the purification section) having less than 100 ppb by weight of the catalyst metal component is treated with a polymeric substrate which includes a polymer with nitrogen-containing heterocyclic repeat units. Specifically preferred resins include vinyl pyrrolidone polymers, vinyl pyridine polymers, and the like.

It has been demonstrated that vinyl pyrrolidone resins will bind rhodium catalyst components, for example, in U.S. Pat. No. 5,466,874 to Scates et al.; whereas, vinyl pyridine resins will likewise bind rhodium catalyst components as described in U.S. Pat. No. 5,155,261 to Marston et al. The '874 and '261 patents are incorporated herein by reference.

The terminology "pyridine ring-containing polymer", "pyridine polymer" and the like used herein is intended to refer to a polymer containing substituted or non-substituted pyridine rings or substituted or non-substituted, pyridine-containing polycondensed rings such as quinoline rings. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of vinylpyridine with styrene, vinylbenzene and divinylbenzene, copolymers of vinylmethylpyridine and divinylbenzene and/or copolymers of vinylpyridine, methyl acrylate and ethyl diacrylate. Suitable poly(vinyl pyridine)polymers are available from Reilly Industries, Indianapolis, Ind. Suitable polymers are also described in U.S. Pat. No. 5,334,755 to Yoneda et al., the disclosure of which is incorporated herein by reference. Relatively high levels of crosslinking in the polymer is most preferred to maintain physical stability and limit solubility of the polymer.

The terminology "pyrrolidone ring-containing polymer", pyrrolidone polymer and the like used herein is intended to refer to a polymer containing substituted or non-substituted pyrrolidone rings. Typical examples of insoluble, pyrrolidone ring-containing polymer include those obtained by reaction of vinyl pyrrolidone with a di-vinyl monomer such as a co-polymer of a vinyl pyrrolidone and divinyl benzene. Pyrrolidone polymers are discussed in U.S. Pat. No. 5,466,874 of Scates et al. as well as U.S. Pat. Nos. 5,286,826; 4,786,699 and 4,139,688, the disclosures of which are incorporated herein by reference.

It is desirable that the polymer with nitrogen-containing heterocyclic ring repeating should be crosslinked by at least 10%, preferably at least 15% or 20% and up to 75%. A degree of crosslinking below 10% is disadvantageous because the mechanical strength of the polymer may degrade during use. However, as the degree of crosslinking increases, the availability and number of reactive functional groups on the polymer decrease. A maximum degree of crosslinking of 50 or 60 percent is then preferred. The term "degree of crosslinking" used herein is intended to refer to the content, in terms of % by weight, of the divinyl monomer, for example.

A pyridine or pyrrolidone insoluble polymer may be in the free base or N-oxide form or quaternized form. Likewise, the polymers may include alkylated vinyl pyridine or alkylated vinyl pyrrolidone polymer such as are available from ISP, Wayne, N.J. Suitable densely crosslinked, highly porous crospovidone polymers (vinyl pyrrolidones) are also available from ISP. The insoluble, pyridine or pyrrolidone ring-containing polymer is preferably in a bead or particulate granular form, preferably in a spherical form, having a particle diameter of 0.01-2 mm, preferably 0.1-1 mm, more preferably 0.25-0.7 mm. Commercially available pyridine-containing polymers such as Reillex®-425 (product of Reilly Industries, Indianapolis, Ind.) and KEX-316, KeX-501 and KEX-212 (products of Koei Chemical Co., Ltd.) may be suitably used for the purpose of the present invention.

The above-noted resins are unexpectedly effective in sequestering catalyst metals from the partially purified product and are believed to operate by way of chelation as well as ion-exchange, given the diverse conditions and likely very diverse catalyst metal species in the purification train. On the outlet of the light ends column, there may be sufficient methyl iodide introduced to a purification bed to partially or fully quaternize the resin making it effective to remove anionic species; however, at the outlet of the dehydration column it is unlikely any substantial portion of the resin becomes quaternized, yet the resin is still very effective. The resin may be predominantly in the quaternized, predominantly in the N-oxide or predominantly in the free base form, yet remain effective.

The apparently universal effectiveness of the nitrogen heterocycle resins in sequestering catalyst species at such trace ppb concentrations and the overall effectiveness of the inventive process is surprising. The resins are so effective that the beds may be operated at relatively low residence times, minimizing the required size of the bed and thus capital costs. Generally speaking, in operation of the invention, a purified process stream is generated and sent through a polymer bed, where the process stream includes the catalyst metal in low concentrations, i.e., less than 100 ppb by weight. For example, in an acetic acid process, the light ends side stream includes from about 1 to 50 ppb by weight of Group VIII metal, and more typically from 2 to 40 ppb or from 5 to 30 ppb under steady state conditions.

The amount of entrained catalyst in the process stream sent to the purification system depends greatly upon the specific equipment employed and its effectiveness to minimize entrainment. However, it has been found that even the best mechanical technology leaves trace levels of catalyst metals in the purified process stream which are subsequently lost. Further, in the case of iridium catalyst, it is known that some iridium species are volatile and undesirably distill into the purification system.

Figure 1:
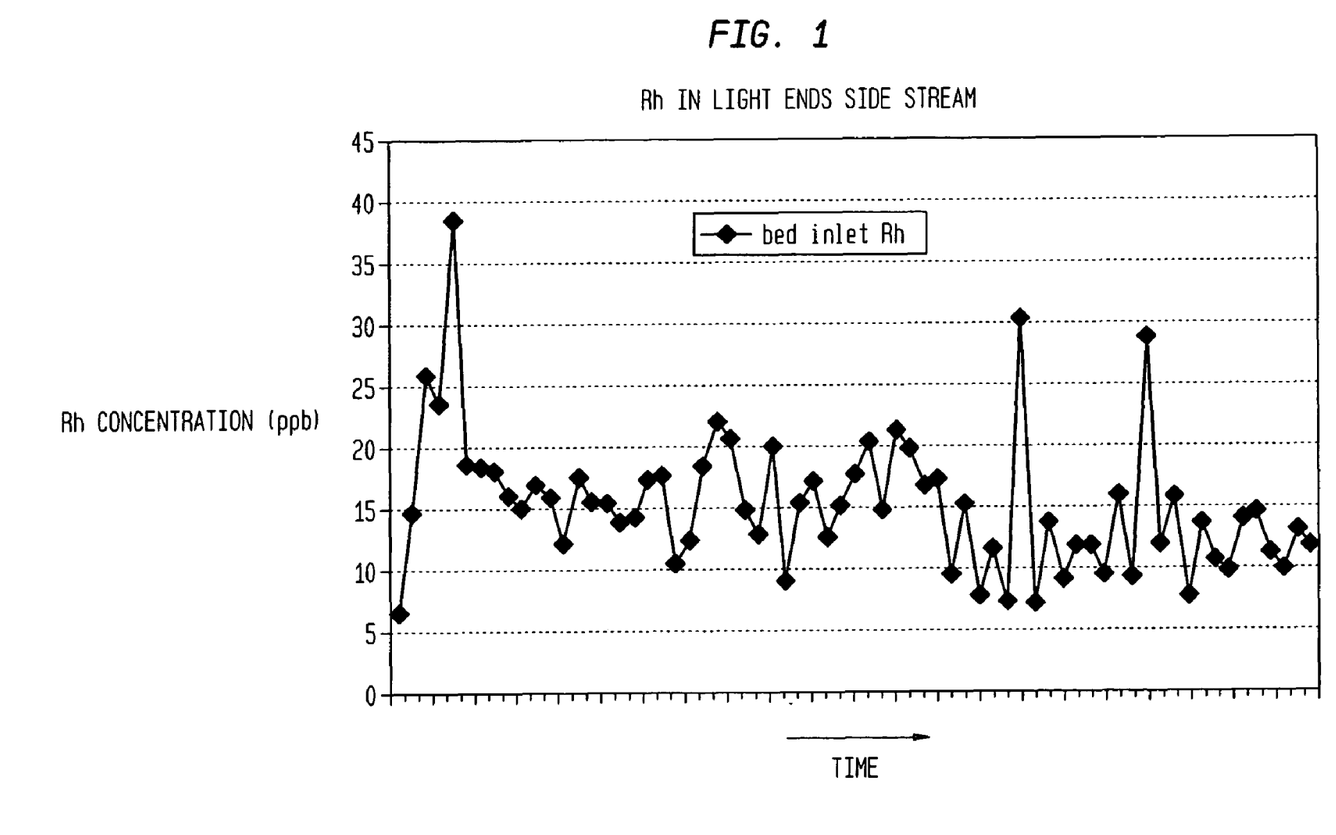
FIG. 1 is a graph which shows typical levels of entrained rhodium catalyst in a light ends side stream of an acetic acid process.

FIG. 1 of this application shows the rhodium concentration of a typical light ends process stream, taken over a period more than six (6) months) from the side of the column in an acetic acid process. As can be seen, the concentration varies, yet remains in the ppb range and does not exceed 40 ppb over an extended period of time; although when a process upset occurs, levels may be higher. For process streams which are further downstream, for example, the residue stream from the dehydration column, the catalyst metal concentration is even lower; typical amounts are from about 2 to 15 ppb.

In accordance with the invention, entrained or volatile catalyst species are sequestered from the process stream and immobilized on the resin, which may be provided as a particulate polymer resin bed. Generally the polymer is effective to remove at least about 50% of the catalyst metal from the process stream, and more preferably removes at least about 75% or at least about 95%. Preferably, the polymer substantially quantifiably removes catalyst metal from the stream, such that the outlet from the polymer resin bed contains less than about 2 ppb of Group VIII catalyst metal. Smaller beds are generally preferred from a cost-perspective.

The metal catalyst may be subsequently recovered by digesting the polymer, e.g., by incineration, or by other known processes where the polymer is spared, such as using conventional ion-exchange regeneration techniques with ammonium salts, sulfuric acid or hydrochloric acid and subsequently recovering the metal from the regeneration liquor. More preferably, sequestered catalyst metal is removed from the resin by using a regenerant including a regenerant solvent and one or more regenerating agents compatible with the reaction system. The recovered catalyst metal can then be directly recycled to the reactor and the resin re-used to improve system economics and reduce environmental impact. Suitable regenerant solvents for regenerating the resin include water, acetic acid, methyl acetate, methyl formate methanol and mixtures thereof. Suitable regenerating agents include soluble Group IA and Group IIA metal salts and hydroxides as well as hydrogen halides. Exemplary regenerant compositions for regenerating the resin bed thus include aqueous solutions of: lithium acetate; lithium carbonate; lithium hydroxide; lithium iodide; hydrogen iodide; potassium hydroxide; potassium iodide; sodium acetate; sodium iodide; sodium carbonate; sodium hydroxide and so forth.

The resin bed is regenerated by treatment with adequate amounts of such compositions. The regenerant liquor recovered after regenerating the bed may then be recycled directly to the reactor; that is, without isolating the catalyst metal therefrom, provided the regenerant liquor is compatible with the reaction mixture. Preferably, the regenerant liquor contains components normally added to the reactor during a manufacturing campaign. Typically, such components are HI, group IA or IIA iodide salts which are added to the reactor to make up for entrainment or other fugitive losses of material. Optionally, some of the regenerant solvent may be removed prior to recycle into the system.

Figure 2:
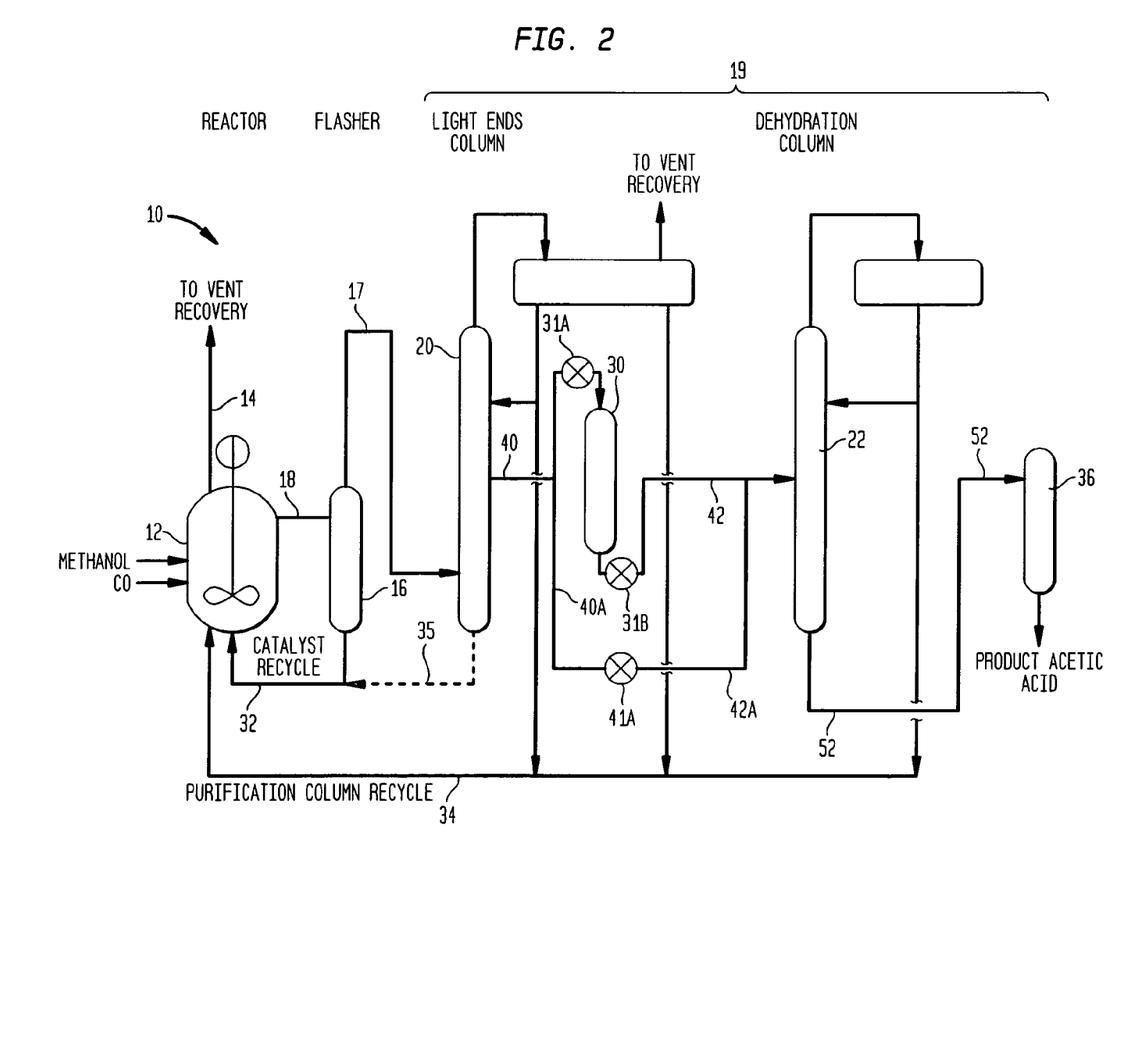
FIG. 2 is a schematic diagram illustrating one embodiment of a carbonylation system which may be used in connection with the present invention where a particulate polymer resin bed is placed on a side stream of the light ends column.

The present invention is further appreciated by reference to FIG. 2 which is a schematic diagram illustrating a typical carbonylation process which includes a catalyst sequestering system of the invention. In FIG. 2 there is shown a carbonylation system 10 including a reactor 12 provided with a vent 14. Reactor 12 is coupled to a flasher 16 by way of a conduit 18. The flasher, in turn, is coupled to a purification section 19 which comprises generally a light ends column 20, a dehydration column 22 and a strong acid, silver-exchanged cation ion-exchange resin bed 36 which removes iodides from the product. Instead of a silver-exchanged, strong acid cation ion-exchange resin, it has been reported that anion ion-exchange resin can be used to remove iodides. See British Patent No. G 2112394A, as well as U.S. Pat. No. 5,416,237, Col. 7, lines 54+, which teaches the use of 4-vinylpyridine resins for iodide removal.

A gaseous purge stream is typically vented from the head of the reactor to prevent buildup of gaseous by-products such as methane, carbon dioxide and hydrogen and to maintain a set carbon monoxide partial pressure at a given total reactor pressure. Optionally (as illustrated in Chinese Patent No. ZL92108244.4), a so-called "converter" reactor can be employed which is located between the reactor and flasher vessel shown in FIGS. 2 and 3. The "converter" produces a vent stream comprising gaseous components which are typically scrubbed with a compatible solvent to recover components such as methyl iodide and methyl acetate. The gaseous purge streams from the reactor and converter can be combined or scrubbed separately and are typically scrubbed with either acetic acid, methanol or mixtures of acetic acid and methanol to prevent loss of low boiling components such as methyl iodide from the process. If methanol is used as the vent scrub liquid solvent, the enriched methanol from the scrubbing system is typically returned to the process by combining with the fresh methanol feeding the carbonylation reactor—although it can also be returned into any of the streams that recycle back to the reactor such as the flasher residue or light ends or dehydration column overhead streams. If acetic acid is used as the vent scrub liquid solvent, the enriched acetic acid from the scrubbing system is typically stripped of absorbed light ends and the resulting lean acetic acid is recycled back to the absorbing step. The light end components stripped from the enriched acetic acid scrubbing solvent can be returned to the main process directly or indirectly in several different locations including the reactor, flasher, or purification columns. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well within the scope of the present invention as will be appreciated from the appended claims and the description which follows.

In accordance with a first illustrative embodiment of the invention, there is provided a fixed bed of pyrrolidone or pyridine resin in granular or bead form indicated at 30 on the purified process stream 40 from the light ends column.

As will be appreciated by one of skill in the art, the different chemical environments encountered in the purification train may require different metallurgy. For example, a resin bed at the outlet of the light ends column will likely require a zirconium vessel due to the corrosive nature of the process stream, while a vessel of stainless steel may be sufficient for resin beds placed downstream of this dehydration column where conditions are much less corrosive.

Carbon monoxide and methanol are introduced continuously into reactor 12 with adequate mixing at a high carbon monoxide partial pressure. The non-condensable bi-products are vented from the reactor to maintain an optimum carbon monoxide partial pressure. The reactor off gas is treated to recover reactor condensables, i.e., methyl iodide before flaring. Methanol and carbon monoxide efficiencies are preferably greater than about 98 and 90% respectively. As will be appreciated from the Smith et al. patent noted above, major inefficiencies of the process are the concurrent manufacture of carbon dioxide and hydrogen by way of the water gas shift reaction.

From the reactor, a stream of the reaction mixture is continuously fed via conduit 18 to flasher 16. Through the flasher the product acetic acid and the majority of the light ends (methyl iodide, methyl acetate, water) are separated from the reactor catalyst solution, and the crude process stream 17 is forwarded with dissolved gases to the distillation or purification section 19 in single stage flash. The catalyst solution is recycled to the reactor via conduit 32. Under the process conditions of the flash, rhodium is susceptible to deactivation at the low carbon monoxide partial pressures in the flash vessel, and may be entrained to purification system 19.

The purification of the acetic acid typically includes distillation in a light ends column, a dehydration column, and, optionally, a heavy ends column. The crude vapor process stream 17 from the flasher is fed into the light ends column 20. Methyl iodide, methyl acetate, and a portion of the water condense overhead in the light end columns to form two phases (organic and aqueous). Both overhead phases return to the reaction section via recycle line 34. The dissolved gases from the light ends column vent through the distillation section. Before this vent stream is flared, residual light ends are scrubbed and recycled to the process. Optionally, a liquid recycle stream 35 from the light ends column may also be returned to the reactor.

The purified process stream 40 is drawn off the side of the light end column 20 and is fed into a fixed bed 30 containing pyrrolidone, pyridine or other similar nitrogen-containing resin so as to remove the entrained or the volatile Group VIII metal catalyst species present. The concentration of catalyst in the light ends process stream is typically about one or two order of magnitudes lower than the catalyst concentration in the crude vapor stream coming off of the flasher. The exit process stream 42 from the polymer bed is then fed into dehydration column 22. Water and some acetic acid from this column separate and are recycled to the reaction system via recycle line 34 as shown. The purified and dried process stream 52 from the dehydration column 22 feeds resin bed 36 and product is taken therefrom as shown. Carbonylation system 10 uses only 2 purification columns and is preferably operated as described in more detail in U.S. Pat. No. 6,657,078 to Scates et al., entitled "Low Energy Carbonylation Process", the disclosure of which is incorporated herein by reference.

System 10 is optionally provided with a bypass lines 40A, 42A with a valve 41A. Bed 30 has a pair of valves 31A, 31B which can be used to isolate the bed during regeneration or replacement of the resin. For example, during normal operation, valves 31A, 31B are open and valve 41A is closed so that the process stream is treated in resin bed 30. If so desired, some or all of the process stream may be directed through lines 40A, 42A by opening valve 41A and closing, or partially closing, valves 31A, 31B.

In FIG. 2, the product acetic acid is afforded as the residue of the dehydration column as shown.

Figure 3:
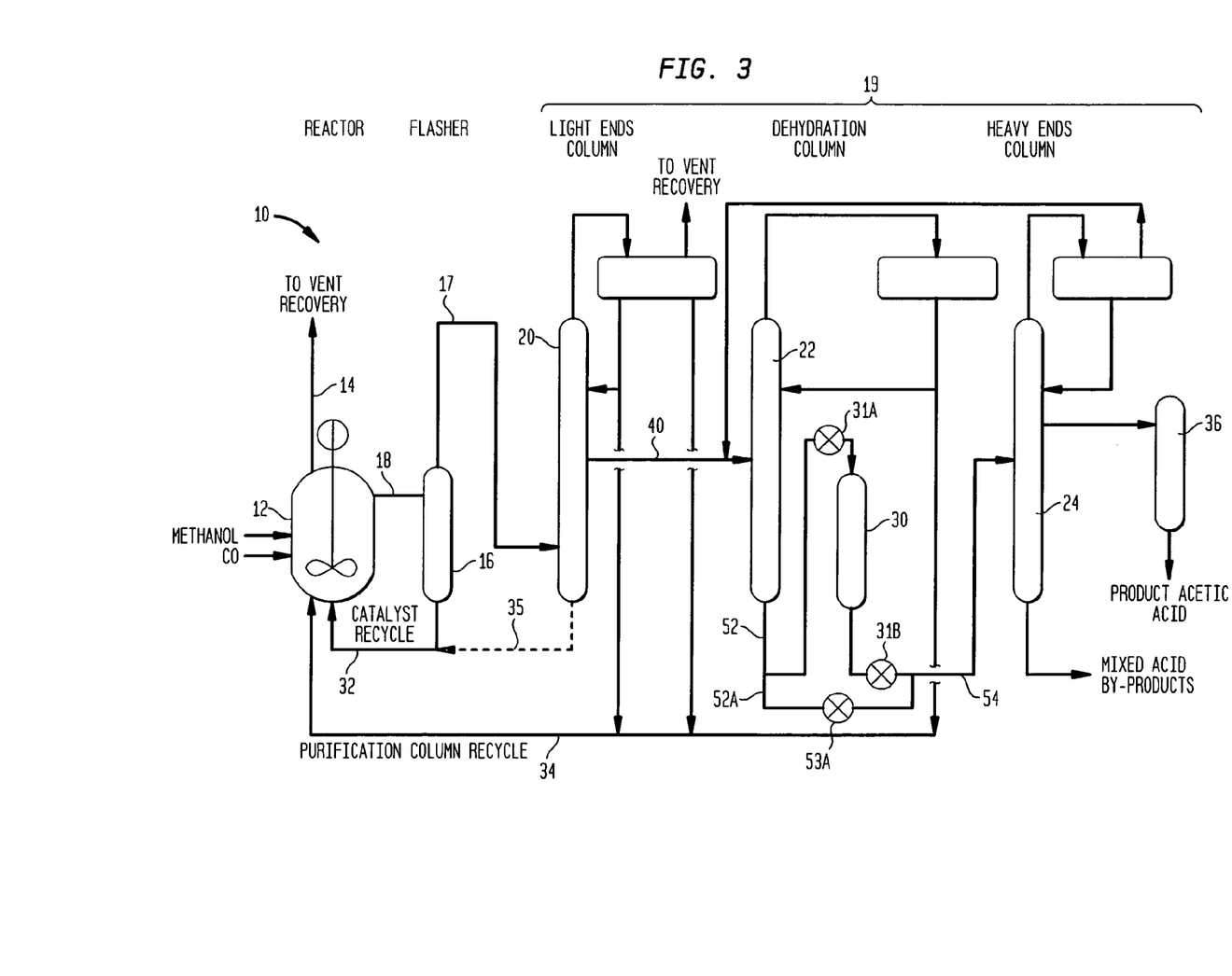
FIG. 3 is a schematic diagram illustrating a second embodiment of a carbonylation system which may be used in connection with the present invention where a particulate polymer resin bed is placed on the residue stream from a dehydration column.

FIG. 3 illustrates another embodiment of the present invention where the process is similar to the one described in connection with FIG. 2, except the catalyst sequestering unit 30 is positioned after the dehydration column 22 and a heavy ends purification column is included. Here, the purified and dried process stream 52 from the dehydration column 22 is fed into polymer bed 30 which contains a resin with nitrogen-containing heterocyclic repeat units. The exit process stream 54 from the polymer bed is then fed into a heavy ends column 24 which, in turn, feeds iodide removal bed 36 via a side drawn from the column.

System 10 of FIG. 3 is likewise optionally provided with a bypass line 52A with a valve 53A. Bed 30 has a pair of valves 31A, 31B which can be used to isolate the bed during regeneration or replacement of the resin, as is noted above.

The following examples are presented to further illustrate and explain the present invention and should not be taken as limiting the invention in any way.

EXAMPLES

In the following examples, a resin bed containing Reillex-425 was installed on the side stream of the light ends column (feed to the dehydration column) in a commercial carbonylation process for making acetic acid, e.g., FIG. 2 arrangement. The amount of rhodium metal going both into and out of the resin bed was analyzed. From this, the rhodium absorbed by the polymer can be determined, as well as the annualized savings from entrained catalyst which will vary depending upon prices of the precious metal catalyst. The results appear in Table 1, below.

TABLE 1

Absorption Data for Light Ends Side Stream

| Sample | Flow Rate (BV/hour) | Rh inlet (ppb) | Rh outlet (ppb)* | Rh absorbed (ppb) |
|---|---|---|---|---|
| 1 | 7.2 | 14.2 | <1 | 14.2 |
| 2 | 7.2 | 14.8 | <1 | 14.8 |
| 3 | 7.2 | 11.4 | <1 | 11.4 |
| 4 | 7.2 | 10.1 | <1 | 10.1 |
| 5 | 14.4 | 13.3 | <1 | 13.3 |
| 6 | 14.4 | 12.0 | <1 | 12.0 |
| AVERAGE | 9.6 | 12.6 | <1 | 12.6 |

*detection limit of about 1 ppb

Figure 4:
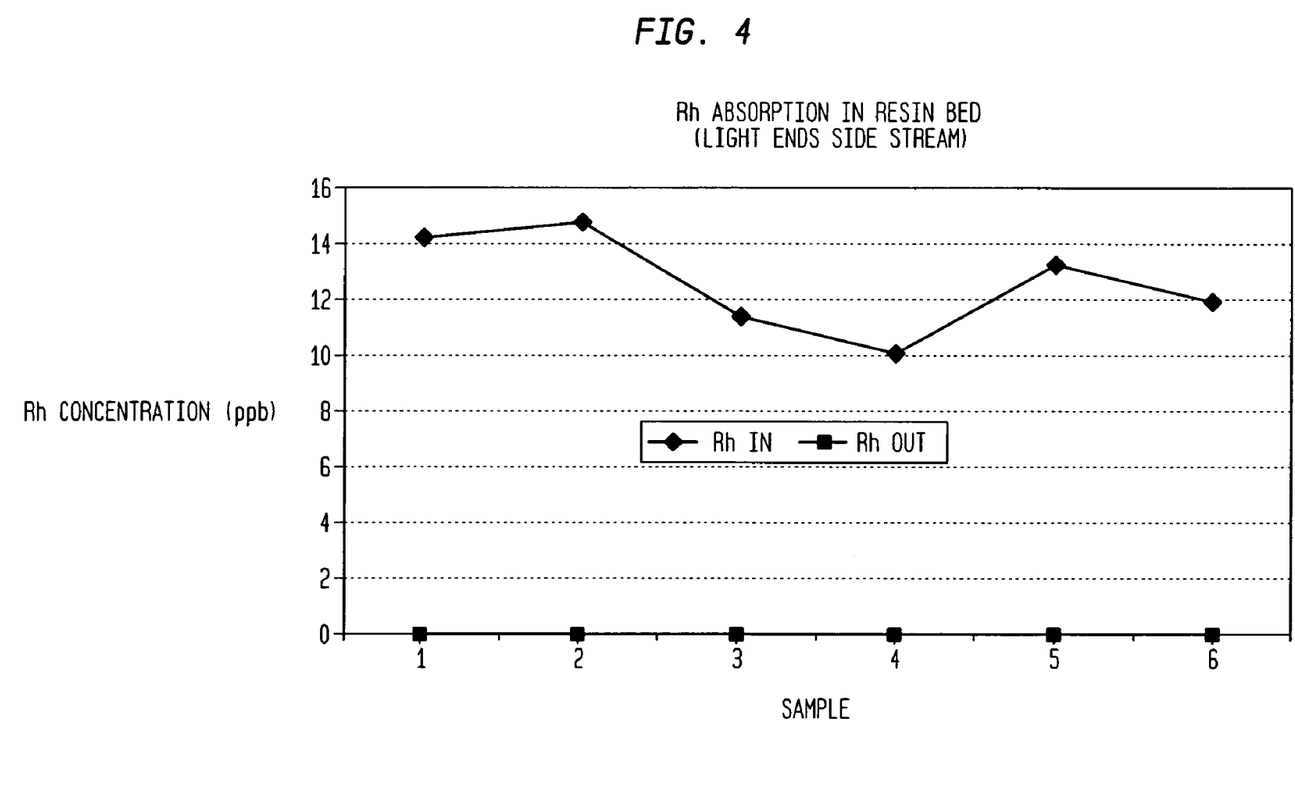
FIG. 4 is a graph showing the absorption of rhodium catalyst in a polymer resin bed placed on a feed stream to a dehydration column.

The above data from the light ends side stream is illustrated in FIG. 4. As can be seen, the polymer resin bed is extremely effective in removing catalyst even when in miniscule concentrations of about 10-15 ppb. Indeed, the amount of metal catalyst remaining in the outlet stream was below detectable limits (below about 1 ppb). The inventive arrangement was subsequently tested at higher flow rates as shown in Table 2 below, where it is seen that removal remained surprisingly efficient.

TABLE 2

Absorption Data at higher Flow

| Sample | Flow Rate (BV/hour) | Rh inlet (ppb) | Rh outlet (ppb)* |
|---|---|---|---|
| 1 | 25 | 21.9 | <1 |
| 2 | 25 | 28.7 | <1 |
| 3 | 42 | 22.2 | <1 |
| 4 | 42 | 22.0 | <1 |
| 5 | 42 | 26.1 | <1 |
| 6 | 42 | 25.4 | <1 |
| 7 | 42 | 21.6 | <1 |
| 8 | 42 | 19.1 | <1 |
| 9 | 42 | 19.4 | <1 |
| 10 | 42 | 18.0 | <1 |
| 11 | 42 | 19.85 | <1 |

*detection limit of about 1 ppb

Next, the resin bed was positioned on the residue process stream of the dehydration column (FIG. 3 arrangement). Here again, the rhodium concentration was measured on the bed inlet stream and the bed outlet stream. The rhodium absorbed is determined, as well as the total cumulative rhodium which would be sequestered on the polymer. The results are shown in Table 3.

TABLE 3

Absorption Data for Residue of Dehydration Column

| Sample | Rh Inlet (ppb) | Rh* Outlet (ppb) | Rh absorbed (ppb) | Flow Rate (BV/hr) | Bed Temp. (° F.) |
|---|---|---|---|---|---|
| 1 | 2.5 | <1 | 2.5 | 7.44 | 175 |
| 2 | 2.8 | <1 | 2.8 | 7.44 | 175 |
| 3 | 3.5 | <1 | 3.5 | 7.44 | 175 |
| 4 | 3.5 | <1 | 3.5 | 7.44 | 175 |
| 5 | 7.6 | <1 | 7.6 | 7.44 | 175 |
| 6 | 8.5 | <1 | 8.5 | 7.44 | 175 |
| 7 | 6.6 | <1 | 6.6 | 7.44 | 175 |
| 8 | 6.7 | <1 | 6.7 | 7.44 | 175 |
| 9 | 6.2 | <1 | 6.2 | 7.44 | 175 |
| 10 | 6.7 | <1 | 6.7 | 7.44 | 175 |
| 11 | 7.1 | <1 | 7.1 | 12.4 | 160 |
| 12 | 7.2 | <1 | 7.2 | 12.4 | 150 |

TABLE 3-continued

Absorption Data for Residue of Dehydration Column

| Sample | Rh Inlet (ppb) | Rh* Outlet (ppb) | Rh absorbed (ppb) | Flow Rate (BV/hr) | Bed Temp. (° F.) |
|---|---|---|---|---|---|
| 13 | 6.6 | <1 | 6.6 | 12.4 | 150 |
| 14 | 7.3 | <1 | 7.3 | 12.4 | 140 |
| 15 | 8.8 | <1 | 8.8 | 12.4 | 150 |
| 16 | 11.0 | <1 | 11.0 | 14.9 | — |
| 17 | 12.7 | <1 | 12.7 | 14.9 | — |
| 18 | 10.8 | <1 | 10.8 | 14.9 | — |
| 19 | 12.0 | <1 | 12.0 | 14.9 | — |

*detection limit of about 1 ppb

Figure 5:
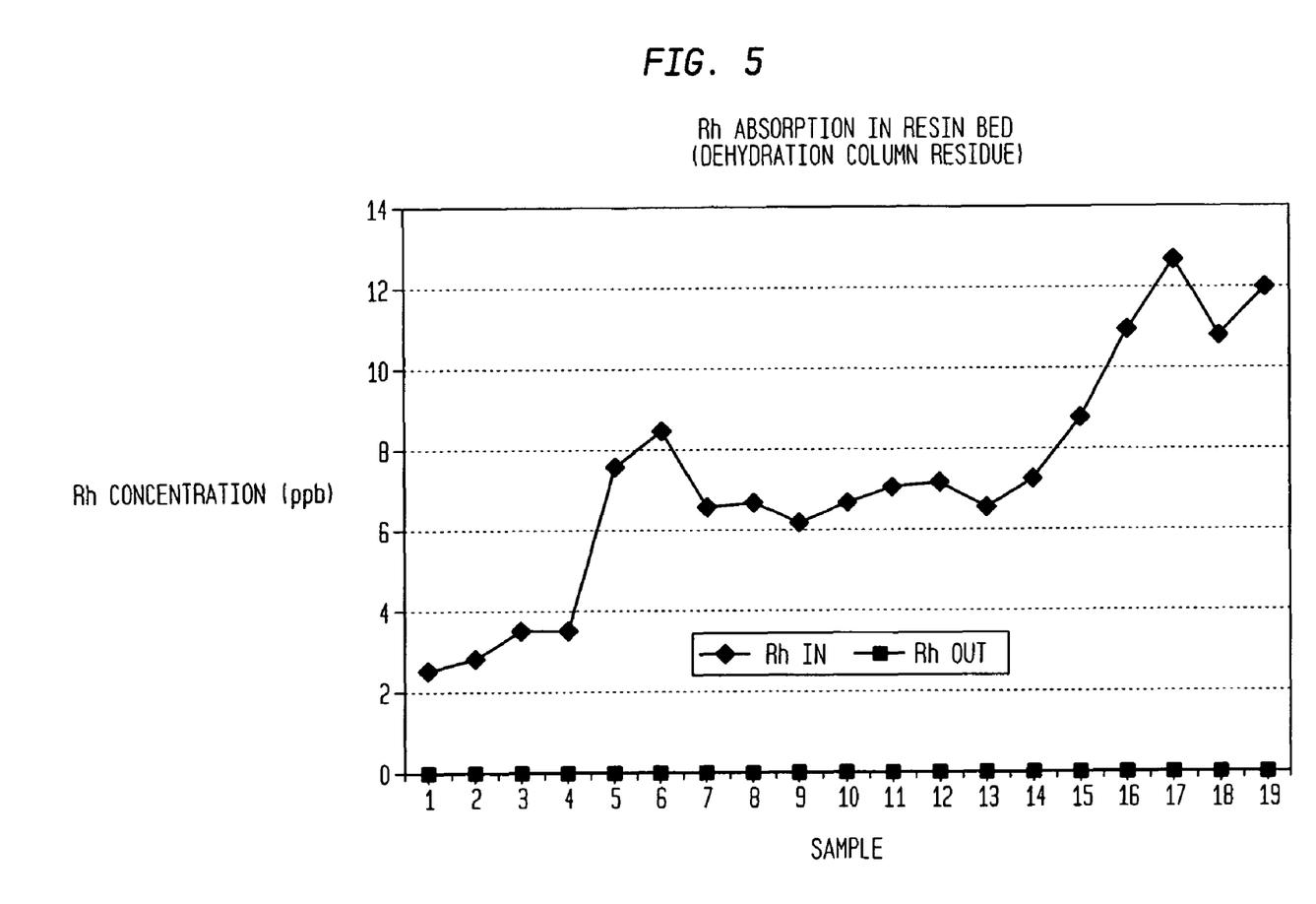
FIG. 5 is a graph illustrating the absorption of rhodium catalyst in a polymer resin bed placed on the residue stream of the dehydration column.

The above data is illustrated graphically in FIG. 5. As with the light ends side stream, the polymeric resin bed is effective to sequester essentially all of the catalyst present.

The invention has been described in detail and illustrated in connection with numerous embodiments. Modifications to specific embodiments within the spirit and scope of the present invention will be readily apparent to those of skill in the art. Such modifications are within the spirit and scope of the present invention which is set forth in the appended claims.

What is claimed is:

1. A carbonylation process comprising: (a) carbonylating a reactant in the presence of a Group VIII metal catalyst and an alkyl halide promoter component to form a carbonylated product reaction mixture in a reactor; (b) separating the stream of the carbonylated product reaction mixture into at least a first liquid recycle stream and a crude process stream; (c) feeding the crude process stream to a light ends column; (d) distilling the crude process stream to remove low boiling components and generate a purified process stream and, optionally, a second liquid recycle stream, wherein steps (a), (b), (c) and (d) are controlled such that the purified process stream has a Group VIII metal content of less than 100 ppb by weight; (e) treating the purified process stream having a Group VIII metal content of less than 100 ppb by weight with a polymer comprising nitrogen-containing heterocyclic repeat units operative to sequester on the polymer the Group VIII catalyst metal present in the purified process stream and (f) recovering the catalyst metal from the polymer by way of a technique selected from digesting the polymer and regenerating the polymer.

2. The carbonylation process according to claim 1, wherein the polymer is operative to remove at least 50% of the Group VIII catalyst metal from the purified process stream.

3. The carbonylation process according to claim 1, wherein the polymer is operative to remove at least 75% of the Group VIII catalyst metal from the purified process stream.

4. The carbonylation process t according to claim 1, wherein the polymer is operative to remove at least 85% of the Group VIII catalyst metal from the purified process stream.

5. The carbonylation process according to claim 1, wherein the polymer is operative to remove at least 90% of the Group VIII catalyst metal from the purified process stream.

6. The carbonylation process according to claim 1, wherein the polymer is operative to remove at least 95% of the Group VIII catalyst metal present in the purified process stream.

7. The carbonylation process according to claim 1, wherein the purified process stream contains less than 50 ppb of Group VIII metal.

8. The carbonylation process according to claim 1, wherein the purified process stream contains less than 40 ppb of Group VIII metal.

9. The carbonylation process according to claim 1, wherein the purified process stream contains from 5 to 30 ppb of Group VIII metal.

10. The carbonylation process according to claim 1, wherein the purified process stream is treated with the polymer at a temperature of at least 75° C.

11. The carbonylation process according to claim 1, wherein the step of treating the purified process stream with a polymer comprising nitrogen-containing heterocyclic repeat units comprises feeding the purified process stream through a resin bed.

12. The carbonylation process according to claim 11, wherein the purified process stream is treated in the resin bed to remove Group VIII catalyst metal at a flow rate of at least 5 BV/hour.

13. The carbonylation process according to claim 12, wherein the purified process stream is treated in the resin bed to remove Group VIII catalyst metal at a flow rate of at least 10 BV/hour.

14. The carbonylation process according to claim 12, wherein the purified process stream is treated in the resin bed to remove Group VIII catalyst metal at a flow rate of at least 20 BV/hour.

15. The carbonylation process according to claim 12, wherein the purified process stream is treated in the resin bed to remove Group VIII catalyst metal at a flow rate of at least 40 BV/hour.

16. The carbonylation process according to claim 12, wherein the purified process stream is treated in the resin bed to remove Group VIII catalyst metal at a flow rate of from about 5 BV/hour to about 100 BV/hour.

17. The carbonylation process according to claim 1, wherein the nitrogen-containing polymer is predominantly in the quaternized form.

18. The carbonylation process according to claim 1, wherein the nitrogen-containing polymer is predominantly in the free-base form.

19. The carbonylation process according to claim 1, wherein the nitrogen-containing polymer is predominantly in the N-oxide form.

20. A carbonylation process for producing acetic acid comprising: (a) carbonylating methanol or its reactive derivatives in the presence of water, a catalyst selected from rhodium catalysts, iridium catalysts and mixtures thereof, and a methyl iodide promoter to form an acetic acid reaction mixture in a reactor; (b) separating the stream of the acetic acid reaction mixture into at least a first liquid recycle stream and a crude process stream; (c) feeding the crude process stream to a light ends column; (d) distilling the crude process stream to remove low boiling components and generate a purified process stream and, optionally, a second liquid recycle stream, wherein steps (a), (b), (c) and (d) are controlled such that the purified process stream has a catalyst metal content of less than 100 ppb by weight; (e) treating the purified process stream having a catalyst metal content of less than 100 ppb by weight, with a polymer comprising nitrogen-containing heterocyclic repeat units operative to sequester, on the polymer, catalyst metal present in the purified process stream and (f) recovering the catalyst metal from the polymer by way of a technique selected from digesting the polymer and regenerating the polymer.

21. The process according to claim 20, further comprising the step of distilling the purified process stream in a second distillation column to remove water and generate a purified and dried process stream, prior to treating the purified and dried process stream with the polymer.

22. The method according to claim 20, wherein the reaction mixture includes acetic acid, methyl iodide and methyl acetate.

23. The method according to claim 20, wherein the catalyst metal is recovered from the polymer with a regenerant composition which is compatible with the reaction mixture and further comprising the step of directly recycling the recovered catalyst metal to the reaction mixture.

24. In a methanol carbonylation process including generally carbonylating a reactant using a supported Group VIII metal catalyst, the improvement comprising the sequential steps of: (a) generating a process stream such that it has a Group VIII metal content of less than 100 ppb by weight; and (b) treating the process stream having a Group VIII metal content of less than 100 ppb by weight with a polymer comprising nitrogen-containing heterocyclic repeat units operative to sequester on the polymer the Group VIII catalyst metal present in the process stream and recovering the Group VIII catalyst metal from the polymer by way of a technique selected from digesting the polymer and regenerating the polymer.

25. In a methanol carbonylation process including generally carbonylating a reactant in the presence of a Group VIII metal catalyst and an alkyl halide promoter in a reaction mixture and purifying the reaction mixture to generate a process stream containing acetic acid, the improvement comprising the sequential steps of: (a) purifying the process stream such that it has a Group VIII metal content of less than 100 ppb by weight; (b) treating the purified process stream having a Group VIII metal content of less than 100 ppb by weight with a polymer comprising nitrogen-containing heterocyclic repeat units operative to sequester on the polymer of the Group VIII catalyst metal present in the purified process stream; and (c) recovering the Group VIII catalyst metal from the polymer.

26. A carbonylation process with catalyst metal recycle comprising: (a) carbonylating a carbonylatable reactant in the presence of a Group VIII metal catalyst and an alkyl halide promoter to form a carbonylated product reaction mixture; (b) supplying the reaction mixture to a flash system and generating a process stream which contains entrained Group VIII catalyst metal; (c) feeding the process stream to a purification system including a resin bed of polymer provided with nitrogen-containing heterocyclic repeat units operative to sequester on the polymer entrained Group VIII catalyst metal: (d) periodically isolating the resin bed from the purification system and regenerating the resin with a regenerant composition to recover the sequestered catalyst metal in a regeneration liquor as well as regenerate the resin; the regenerant composition including a regenerant solvent and a regenerating agent selected such that regeneration liquor is compatible with the reaction mixture; and (e) directly recycling the recovered Group VIII catalyst metal to the reaction mixture with regeneration liquor.

27. The process according to claim 26, wherein the reaction mixture comprises a liquid selected from water, acetic acid and methyl iodide and the regenerant solvent comprises a liquid selected from water, acetic acid and methanol.

28. The process according to claim 26, wherein the reaction mixture and regenerant composition are aqueous compositions.

29. The process according to claim 26, wherein the regenerant composition comprises a regenerating agent selected from: soluble Group IA and Group IIA metal salts; Group IA and Group IIA metal hydroxides; and hydrogen halides.

30. The process according to claim 26, wherein the regenerant composition is an aqueous composition including at least one of the following regenerating agents: lithium acetate; lithium carbonate; lithium hydroxide; lithium iodide; hydrogen iodide; potassium hydroxide; potassium iodide; sodium acetate; sodium iodide; sodium carbonate; sodium acetate; and sodium hydroxide.

* * * * *